United States Patent
Belgoroski

(10) Patent No.: US 10,950,354 B1
(45) Date of Patent: Mar. 16, 2021

(54) COMPUTING SYSTEM FOR PHARMACOGENOMICS

(71) Applicant: Allscripts Software, LLC, Raleigh, NC (US)

(72) Inventor: Yotam Belgoroski, Dimona (IL)

(73) Assignee: ALLSCRIPTS SOFTWARE, LLC, Raleigh, NC (US)

( * ) Notice: Subject to any disclaimer, the term of this patent is extended or adjusted under 35 U.S.C. 154(b) by 256 days.

(21) Appl. No.: 15/911,038

(22) Filed: Mar. 2, 2018

(51) Int. Cl.
*G16H 50/50* (2018.01)
*G16H 80/00* (2018.01)
*G16H 10/60* (2018.01)

(52) U.S. Cl.
CPC .............. *G16H 50/50* (2018.01); *G16H 10/60* (2018.01); *G16H 80/00* (2018.01)

(58) Field of Classification Search
CPC .... G06F 1/00–2221/2153; G16H 10/00–80/00
See application file for complete search history.

(56) References Cited

U.S. PATENT DOCUMENTS

| | | | | |
|---|---|---|---|---|
| 6,488,669 | B1 * | 12/2002 | Sagona | B01L 3/508 600/584 |
| 8,401,801 | B2 * | 3/2013 | Mrazek | C12Q 1/6883 702/20 |
| 10,223,501 | B1 * | 3/2019 | Schneider | G06F 19/328 |
| 2002/0052761 | A1 | 5/2002 | Fey et al. | |
| 2002/0147616 | A1 * | 10/2002 | Pollard | G06F 19/325 705/3 |
| 2002/0187483 | A1 | 12/2002 | Hoffman et al. | |
| 2003/0040002 | A1 * | 2/2003 | Ledley | G06Q 50/22 435/6.11 |

(Continued)

FOREIGN PATENT DOCUMENTS

EP 3249561 A1 * 11/2017 ............. G16H 10/40

OTHER PUBLICATIONS

Website entitled "Genetic Testing Registry (GTR)—NCBI" at www.ncbi.nlm.nih.gov/gtr as captured by web.archive.org on Jan. 7, 2017. (Year: 2017).*

(Continued)

*Primary Examiner* — Elaine Gort
*Assistant Examiner* — Jonathon A. Szumny
(74) *Attorney, Agent, or Firm* — Medley, Behrens & Lewis, LLC

(57) ABSTRACT

A supplement application for ordering genetic tests is disclosed herein. The supplement application receives an identifier for a medication for a patient and an identifier for the patient from an electronic health records application. The supplement application retrieves an identifier for a variant form of a gene based on the identifier for the medication. The variant form of the gene is known to have an interaction with the medication. When the supplement application determines that the patient has failed to undergo a genetic test for the variant form of the gene, the supplement application retrieves an identifier for a genetic laboratory that offers the genetic test. The supplement application then constructs an order for the genetic test using the identifier for the patient, the identifier for the variant form of the gene, and the identifier for the genetic laboratory and transmits the order to a genetic laboratory computing device.

20 Claims, 6 Drawing Sheets

(56) References Cited

U.S. PATENT DOCUMENTS

| | | | |
|---|---|---|---|
| 2003/0073124 A1* | 4/2003 | Bowman | G16H 10/40 435/6.11 |
| 2003/0104453 A1 | 6/2003 | Pickar et al. | |
| 2003/0113756 A1 | 6/2003 | Mertz | |
| 2003/0217037 A1* | 11/2003 | Bicker | G06F 21/6254 |
| 2006/0036619 A1* | 2/2006 | Fuerst | G06Q 10/10 |
| 2008/0195326 A1* | 8/2008 | Munzer | G06O 30/04 702/20 |
| 2009/0094059 A1 | 4/2009 | Coleman et al. | |
| 2010/0174505 A1* | 7/2010 | Abraham-Fuchs | G16H 10/60 702/108 |
| 2011/0082867 A1* | 4/2011 | Bruns | G16B 20/00 707/748 |
| 2011/0113002 A1* | 5/2011 | Kane | G16H 50/30 706/50 |
| 2012/0231959 A1* | 9/2012 | Elton | G06O 50/22 506/2 |
| 2012/0323600 A1* | 12/2012 | Plante | G06O 50/22 705/3 |
| 2013/0268290 A1* | 10/2013 | Jackson | G16B 50/00 705/2 |
| 2014/0222400 A1* | 8/2014 | Coleman | G16C 20/30 703/2 |
| 2014/0244309 A1* | 8/2014 | Francois | G06Q 10/10 705/3 |
| 2014/0316821 A1* | 10/2014 | Sheffield | G06Q 50/22 705/3 |
| 2015/0154375 A1* | 6/2015 | Rosenblatt | G06F 19/3456 705/3 |
| 2016/0070881 A1* | 3/2016 | Millican, III | G16H 10/60 705/3 |
| 2016/0224760 A1* | 8/2016 | Petak | G06F 19/3481 |
| 2016/0239636 A1* | 8/2016 | O'Donnell | G16B 50/00 |
| 2017/0018007 A1* | 1/2017 | DeFrank | G06Q 30/0262 |
| 2018/0135122 A1* | 5/2018 | Hilden | G16B 20/00 |
| 2018/0330824 A1* | 11/2018 | Athey | G16B 30/00 |
| 2019/0244688 A1* | 8/2019 | Wilson | G16H 10/40 |

OTHER PUBLICATIONS

Formal Drawings filed on Aug. 12, 2016 in U.S. Appl. No. 14/345,365, corresponding to U.S. Patent App. Pub. No. 2014/0316821. (Year: 2016).*

* cited by examiner

| PATIENT DETAILS | | 300 ⬅ | | | | 302 |
|---|---|---|---|---|---|---|
| HOME 304 | PHARMACOGENOMICS PROFILE – MEDICATIONS | | | | | 314 |
| PHARMACOGENOMICS PROFILE 306 | MEDICATIONS | GENES TESTED | TEST DETAILS | | | |
| GENETIC TEST RESULTS 308 | CURRENT (4) | PAST (5) | ALL (9) | | | |
| ORDERS 310 | !!! | MEDICATION 1<br>GENE VARIANT 1C – SIGNIFICANT ALTERED RESPONSE | | VIEW GUIDELINE > | | |
| | ! | MEDICATION 2<br>GENE VARIANT 2B – ALTERED RESPONSE | | VIEW GUIDELINE > | | |
| | ? | MEDICATION 3<br>MISSING GENETIC TEST RESULTS – TEST AVAILABLE | | | | |
| | ✓ | MEDICATION 4<br>GENE VARIANT 4A – NORMAL RESPONSE | | | | |
| | • • • | | | | | |
| | | | | ORDER GENETIC TESTS 312 | | |

FIG. 3

COMPUTING SYSTEM FOR PHARMACOGENOMICS

BACKGROUND

Electronic health record applications (EHRs) are computer-executable applications utilized in healthcare environments. EHRs are generally configured to perform various tasks related to healthcare including patient intake tasks, insurance processing tasks, billing tasks, prescription generation tasks, health record maintenance tasks, and so forth. Some EHRs are configured to present information to a healthcare worker relating to medications that are taken by or will be taken by a patient. For instance, an EHR may present dosage information, allergy interactions, usage guidelines, etc.

Some medications are known to have interactions with gene variants in the human genome. For instance, a gene in the human genome may have many different potential variants. Many of the variants may not impact how a medication is processed by a patient. However, some variants may impact how medication is processed by the patient. For example, when the patient possesses a gene variant, the gene variant may cause the medication to be less effective for the patient as compared to a person who does not have the gene variant. Healthcare workers often prescribe medications without regard to genetics of a patient as healthcare workers are not geneticists and often lack genetic knowledge.

Conventional EHRs have generally not been configured to present information regarding medication-genetic interactions. Furthermore, conventional EHRs have generally not been configured to order genetic tests for patients. Thus, if a healthcare worker wishes to ascertain whether a patient has a gene variant that may impact how the patient metabolizes a medication and/or when the healthcare worker wishes to order a genetic test to ascertain whether the patient has the variant, a conventional EHR is not configured to assist the healthcare worker with such tasks. Instead, another computer-executable application must be initiated on a computing device, must accept input from the healthcare worker (which invites user error, as the healthcare worker must type information about the patient, the gene, and so forth into the another application), and then be provided with the results.

SUMMARY

The following is a brief summary of subject matter that is described in greater detail herein. This summary is not intended to be limiting as to the scope of the claims.

Described herein are various technologies pertaining to a computer-executable supplement application that can generate an order for a genetic test for a patient, wherein the genetic test tests whether a patient has a variant form of a gene that has an interaction with a medication of the patient. The supplement application is a distributed application that includes server-side functionality (server supplement application) and client-side functionality (client-side functionality). The supplement application is in communication with an electronic health records application (EHR), and is configured to transmit data to the EHR that informs a healthcare worker that a medication being taken by the patient is associated with a drug-gene interaction (e.g., patients process the drug differently depending upon whether the patients have a gene variant), and further informs the healthcare worker that the patient has not undergone genetic testing for such gene variant.

In operation, the server supplement application executing on a server computing device receives an identifier for a medication for a patient from a server EHR executing on a second server computing device that is in network communication with the server computing device. The medication may be currently prescribed to and taken by the patient. The medication may also be under consideration for prescription to the patient by a healthcare worker. The server supplement application may also receive an identifier for the patient.

Responsive to receiving the identifier for the medication, the server supplement application executes a search over pharmacogenomic data based upon the identifier, wherein the pharmacogenomic data comprises identifiers for medications and identities of genes that are mapped to the medications, wherein a gene mapped to a medication in the pharmacogenomic data indicates that humans may process the medication differently depending upon whether or not the humans have a variant in the gene. Thus, search results returned from the search comprise an identifier for a gene that is known to be associated with different human interactions with the medication. In another example, the search results can comprise an identifier for a variant of the gene that is known to be associated with a particular interaction with the medication. The pharmacogenomic data may be stored in a data store accessible to the server supplement application.

The server supplement application then compares the identifier for the gene (and optionally the identifier for the variant) with genetic test data for the patient, wherein the genetic test data for the patient identifies genes and/or variants of genes for which genetic testing has been conducted for the patient. In an example, based upon this comparison, the server supplement application determines that the patient has not yet undergone a genetic test for the variant of the gene. As noted above, this can be determined by executing a second search based on the identifier for the gene and/or the variant of the gene over genetic data for the patient ("patient genetic data"). There are two possible outcomes of the second search: 1) an indication that a genetic test for the gene (and gene variant) has been performed for the patient; or 2) an indication that the genetic test for the gene (and gene variant) has not been performed for the patient. When the genetic test for the gene (and gene variant) has been performed for the patient, the patient genetic data indicates whether the patient possesses the gene variant. When the patient possesses the gene variant, the server supplement application can cause a warning to be presented on a display of a client computing device, wherein the warning can include an advisement to the healthcare worker that the patient is not to take the medication, and can optionally cause alternative medications to the medication to be presented on the display. When the patient genetic data indicates that the patient does not possess the gene variant, then the server supplement application can cause graphics to be presented on the display of the client computing device, wherein the graphics indicate to the healthcare worker that it is appropriate for the patient to take the medication.

When the genetic test for the gene (and gene variant) has not been performed for the patient (e.g., the patient genetics data fails to include genetic test results for the gene variant), the server supplement application executes a third search over a list of genetics laboratories based upon the identity of the gene (and/or gene variant), wherein returned search results comprise an identifier for a genetic laboratory that offers a genetic test for the gene and gene variant. The list of genetics laboratories comprises identifiers for genetic laboratories and genetic tests offered by each genetic laboratory. The server supplement application may then construct an order for the genetic test using the identifier for the patient, the identifier for the variant form of the gene, and the identifier for the genetic laboratory. The server supplement application then transmits the order for the genetic test to a genetic laboratory computing device operated by the genetic laboratory that is in network communication with the server computing device.

The server supplement application may repeat the above-described process for each medication taken by the patient and/or potentially prescribed to the patient to ensure genetic tests are ordered for genes and/or gene variants that are involved in known drug-gene interactions with medications that are currently taken or will be taken by the patient.

The above-described technologies present advantages over conventional technologies pertaining to ascertaining gene-drug interactions and ordering genetic tests. For instance, the supplement application described above can receive identifiers for medications that are currently taken by the patient and can automatically ascertain drug-gene interactions using the pharmacogenomic data. Furthermore, the supplement application can also automatically generate orders for genetic tests without requiring manual input from a healthcare worker.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIG. 3 is an exemplary graphical user interface (GUI) presented on a display of a client computing device executing a client supplement application.

DETAILED DESCRIPTION

Figure 1:
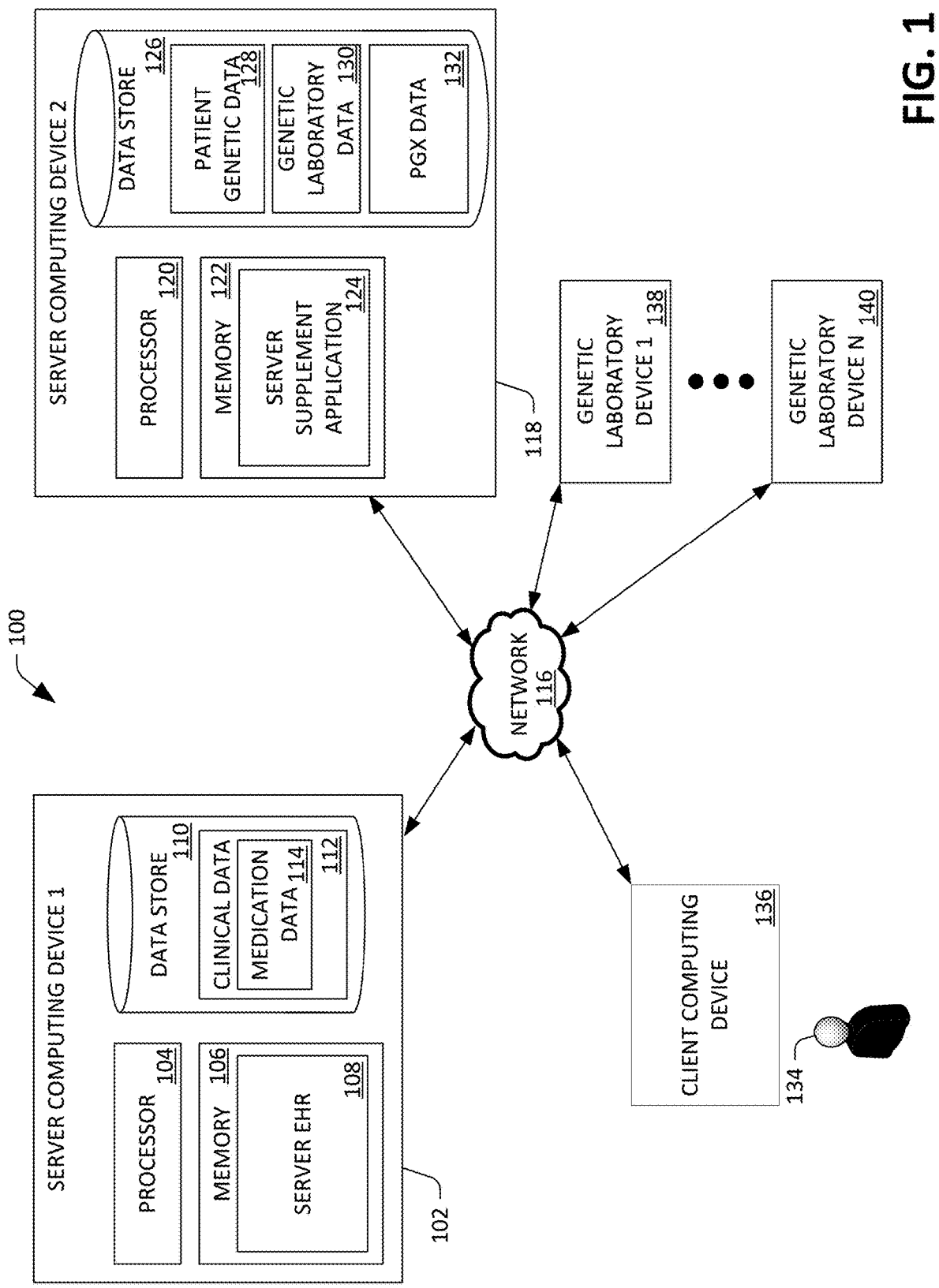
FIG. 1 is a functional block diagram of an exemplary computing system that facilitates ordering a genetic test.

Various technologies pertaining to ordering a genetic test for a variant form of a gene having an interaction with a medication of a patient are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

Further, as used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. Further, as used herein, the term "exemplary" is intended to mean serving as an illustration or example of something, and is not intended to indicate a preference.

As used herein, the phrase "a variant form of the gene has an interaction with a medication" and similar phrases refer to the variant form of the gene being included in a known drug-gene interaction (or a known drug-drug-gene interaction), where the medication comprises the drug, and the variant of the gene is known to be associated with to an undesirable reaction (of a patient) to the drug, such as the inability (of a patient taking the drug) to properly metabolize the drug. With more specificity, the variant form of the gene encodes for a protein, and the variant form of the gene undergoes biological processes which ultimately result in the production of the protein which interacts with the drug such that an undesirable reaction to the drug occurs in a patient that has the variant form of the gene (and hence the protein). In a non-limiting example of an interaction between a gene and a drug, some variants of the CYP2D6 gene are known to be associated with an undesirable reaction (of a patient) to the drug codeine. Furthermore, as used herein, the terms "gene variant" and "variant form of the gene" and similar phrases are to be understood as being interchangeable.

With reference to FIG. 1, an exemplary computing system 100 that facilitates ordering a genetic test for a gene having a variant form that has an interaction with a medication of a patient is illustrated. The computing system 100 includes a first server computing device 102. The first server computing device 102 comprises a processor 104 and memory 106, wherein the memory 106 has a server electronic health records application (server EHR) 108 loaded therein. The server EHR 108 is generally configured to perform a variety of tasks related to patient healthcare in a healthcare facility (e.g., patient intake, prescription generation, patient record creation and maintenance, etc.). The first server computing device 102 also includes a data store 110 that comprises clinical data 112 (amongst other data) about patients, wherein the clinical data 112 is maintained by the server EHR 108. The clinical data 112 can include electronic health records, claims data, patient/disease registries data, health surveys data, and/or clinical trials data. The clinical data 112 also includes medication data 114 for a patient. The medication data 114 includes identifiers for medications that are currently taken by the patient and/or identifiers for medications that have been taken by the patient in the past.

The computing system 100 further includes a second server computing device 118 that is in communication with the first server computing device 102 by way of a network 116 (e.g., the Internet, intranet). The second server computing device 118 comprises a processor 120 and memory 122, wherein the memory 122 has a server supplement application 124 loaded therein. As will be described in greater detail below, the server supplement application 124 is configured to order a genetic test for a patient for a variant form of a gene known to have an interaction with a medication of the patient. The server supplement application 124 is also configured to communicate with a client supplement application 206 executing on a client computing device 136 in order to present identifiers for medications and identifiers for variant forms of genes (or identifiers for genes) that have interactions with the medications within a graphical user interface (GUI) presented on a display of the client computing device 136.

The second server computing device 118 may also comprise a data store 126. The data store 126 may comprise patient genetic data 128, genetic laboratory data 130, and pharmacogenomic data 132 (abbreviated as PGX Data in FIG. 1). The patient genetic data 128 comprises identifiers for variant forms of genes for which the patient has undergone genetic testing. More specifically for each genetic test the patient has undergone, the patient genetic data 128 may specify which variant form of a gene the patient possesses. For instance, the patient genetic data 128 may indicate that the patient has a variant form of a first gene that has an interaction with a first medication, whereas the patient has a variant form of a second gene that does not have an interaction with a second medication. The patient genetic data 128 may include genetic test results themselves or may include data extracted from the genetic test results. While the patient genetic data 128 has been described as including genetic data for a single patient, it is understood that the patient genetic data 128 may include genetic data for many different patients.

The genetic laboratory data 130 comprises identifiers for genetic laboratories and identifiers genetic tests offered by each genetic laboratory in the genetic laboratories. The genetic laboratory data 130 may also comprise additional information relating to genetic laboratories, such as a price for each genetic test offered by the genetic laboratories. Furthermore, the genetic laboratory data 130 may include electronic forms for ordering genetic tests for each genetic laboratory (discussed in greater detail below).

The pharmacogenomic data 132 comprises interactions between a plurality of genes and a plurality of medications (i.e., drug-gene interactions). More specifically, for a medication in the plurality of medications, the pharmacogenomic data 132 may include identifiers for one or more variant forms of a gene (or an identifier for the gene corresponding to the one or more variant forms) that are known to have an interaction with the medication. The pharmacogenomic data 132 may also specify the nature of the interaction. For instance, the pharmacogenomic data 132 may specify that a patient having a variant form of a gene will not metabolize the medication effectively, and hence the medication should not be taken by the patient.

While the patient genetic data 128, the genetic laboratory data 130, and the pharmacogenomic data 132 have been depicted as being retained in the data store 126, other possibilities are contemplated. For instance, the patient genetic data 128, the genetic laboratory data 130, and the pharmacogenomic data 132 may be retained in separate data stores that are accessible to the server supplement application 124. Furthermore, the patient genetic data 128, the genetic laboratory data 130, and the pharmacogenomic data 132 may be maintained by different server computing devices, and the server supplement application 124 may communicate with the different server computing devices in order to access data in the patient genetic data 128, the genetic laboratory data 130, and/or the pharmacogenomic data 132.

The computing system 100 may additionally include a client computing device 136 operated by a healthcare worker 134. The client computing device 136 may be in communication with the first server computing device 102 and the second server computing device 118 by way of the network 116.

Figure 2:
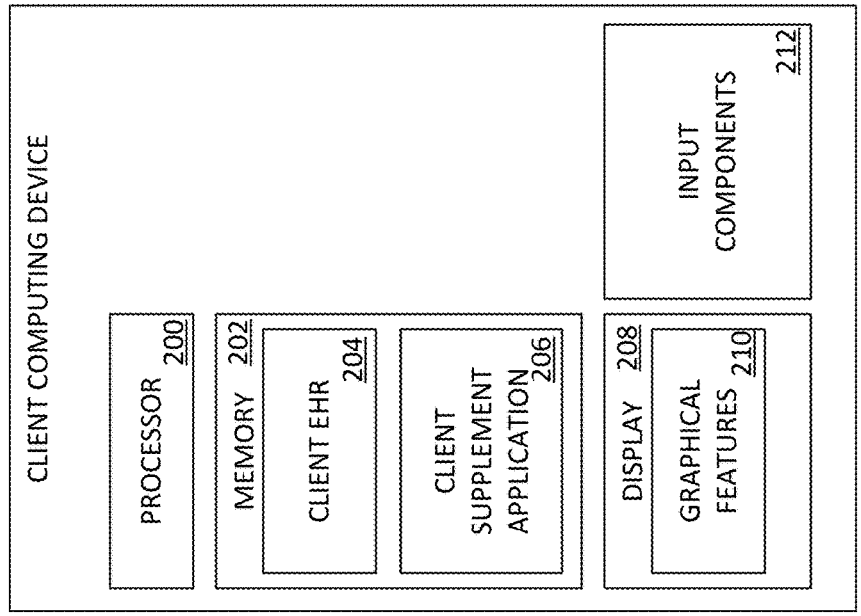
FIG. 2 is a functional block diagram of an exemplary client computing device.

Referring briefly now to FIG. 2, the client computing device 136 comprises a processor 200 and memory 202, wherein the memory 202 has a client electronic health records application (client EHR) 204 and a client supplement application 206 loaded therein. In general, the client EHR 204 is configured to interface with the server EHR 108 executing on the first server computing device 102, thereby providing the healthcare worker 134 with access to functionality of the server EHR 108. The client supplement application 206 is configured to interface with the server supplement application 124 executing on the second server computing device 118, thereby providing the healthcare worker 134 with access to functionality of the server supplement application 124. The client computing device 136 may also comprise a data store (not shown). The data store may comprise a subset of the patient genetic data 128, a subset of the genetic laboratory data 130, and/or a subset of the pharmacogenomic data 132.

Turning back to FIG. 1, the computing system 100 further includes a plurality of genetic laboratory devices 138-140 operated by a plurality of genetic laboratories. For instance, the plurality of genetic laboratory devices 138-140 may be computing devices operated by genetic laboratories. The plurality of genetic laboratory devices 138-140 are in communication with the second server computing device 118 by way of the network 116.

Operation of the computing system 100 is now set forth. In an embodiment, the supplement application operates prospectively and thus it is contemplated that the healthcare worker 134 is contemplating prescribing a medication for a patient. In another embodiment, the supplement application operates retrospectively and thus it is contemplated that the patient is currently taking one or more medications, and the healthcare worker 134 wishes to ascertain whether the patient has undergone a genetic test for a variant form of a gene known to have an interaction with the one or more medications.

The client EHR 204 receives input from the healthcare worker 134 causing the client EHR 204 to transmit an indication to the server EHR 108. The indication may include an identifier for the patient. In an embodiment where the supplement application operates prospectively, the indication may comprise an identifier for a medication that the healthcare worker 134 is contemplating prescribing to the patient. The server EHR 108 then transmits the identifier to the server supplement application 124. In an embodiment where the supplement application operates retrospectively, the indication causes the server EHR 108 to retrieve an identifier for a medication that the patient is currently taking from the medication data 114. The server EHR 108 then transmits the identifier for the medication to the server supplement application 124.

The server supplement application 124 executing on the second server computing device 118 then receives the identifier for the medication from the server EHR 108 executing on the first server computing device 102. The server supplement application 124 may also receive the identifier for the patient. Responsive to receiving the identifier for the medication, the server supplement application 124 then retrieves an identifier for a variant form of a gene known to have an interaction with the medication by executing a first search over the pharmacogenomic data 132. In another example, responsive to receiving the identifier for the medication, the server supplement application 124 may retrieve an identifier for the gene (as opposed to the identifier for the variant of the gene) by executing the first search. The first search is based on the identifier for the medication. In the event that the medication does not have a variant form of a gene known to interact with the medication, the server supplement application 124 can transmit a message to the client supplement application 206 indicating that the medication has no known genetic interactions. The client supplement application 206 can then present the message within a graphical user interface (GUI) shown the display 208 of the client computing device 136.

Responsive to retrieving the identifier for the gene, the server supplement application 124 determines whether the patient has undergone a genetic test for the variant form of the gene known to have the interaction with the medication by executing a second search over the patient genetic data 128. The genetic test indicates whether the patient has the variant form of the gene that has the interaction with the medication. The second search may be based on the identifier for the variant form of the gene or the identifier for the gene.

In the event that the server supplement application 124 determines that the patient has undergone a genetic test for the variant form of the gene, the server supplement application 124 determines whether the patient has the variant form of the gene using the patient genetic data 128. The server supplement application 124 may then transmit the identifier for the medication and an indication of whether the patient has the variant form of the gene to the client supplement application 206. The client supplement application 206 may then display the identifier for the medication and text indicating whether the patient has the variant form of the gene known to have the interaction with the medication within the GUI shown on the display 208 of the client computing device 136. In the event that the patient has the variant form of the gene, the text may include a warning that the patient should not take the medication. In an embodiment, the server supplement application 124 may also be configured to transmit identifiers for alternative medications to the medication to the client supplement application 206, and the client supplement application 206 may present the identifiers for the alternative medications within the GUI.

In the event that the server supplement application 124 determines that the patient has failed to undergo the genetic test for the variant form of the gene (or the genetic test for the gene), the server supplement application 124 retrieves an identifier for a genetic laboratory that offers the genetic test by executing a third search over the genetic laboratory data 130. The third search is based on the identifier for the variant form of the gene or the identifier for the gene. Responsive to retrieving the identifier for the genetic laboratory, the server supplement application 124 constructs an order for the genetic test using the identifier for the patient, the identifier for the variant form of the gene (or the identifier for the gene), and the identifier for the genetic laboratory.

It is understood that many different genetic laboratories may offer the genetic test. In an embodiment, the server supplement application 124 may retrieve identifiers for a plurality of genetic laboratories that offer the genetic test during the third search, as well as information associated with each genetic laboratory (e.g., price for the genetic test). The server supplement application 124 may then transmit the identifiers for each of genetic laboratories in the plurality of genetic laboratories and their associated data to the client supplement application 206. The client supplement application 206 can then present the identifiers for the plurality of genetic laboratories as well as their respective associated data within the GUI for the client supplement application 206. For instance, for each genetic laboratory in the plurality of genetic laboratories, the client supplement application 206 can display an identifier for the genetic laboratory and a price for the genetic test offered by the genetic laboratory within the GUI. The client supplement application 206 can transmit the identifier for a genetic laboratory in the plurality of genetic laboratories (e.g., the genetic laboratory with the best price for the genetic test) to the server supplement application 124 responsive to receiving a selection of the identifier for the genetic laboratory within the GUI. The server supplement application 124 can then construct the order for the genetic test as described above.

In an embodiment, subsequent to determining whether the patient has failed to undergo the genetic test for the variant form of the gene, the server supplement application 124 transmits data to the client supplement application 206. The data causes the client supplement application 206 to present the identifier for the medication, the identifier for the variant form of the gene, and a visual marker within a graphical user interface (GUI) presented on the display 208 of the client computing device 136. The visual marker may indicate that the patient has not yet undergone the genetic test, the patient has undergone the genetic test and has the variant form of the gene known to have the interaction with the medication, or the patient has undergone the genetic test and has a variant form of the gene that is not known to have the interaction with the medication.

In an embodiment, the genetic laboratory data 130 includes electronic forms for genetic laboratories. The server supplement application 124 may retrieve an electronic form for the genetic laboratory during the third search described above. The server supplement application 124 then populates the electronic form for the genetic laboratory using the identifier for the patient, the identifier for the variant of the gene, and the identifier for the genetic laboratory.

Responsive to constructing the order for the genetic test, the server supplement application 124 transmits the order for the genetic test to the genetic laboratory device 138. Sometime later, the patient may then undergo the genetic test and the genetic laboratory may produce genetic test results for the genetic test. The genetic laboratory device 138 can transmit the genetic test results to the server supplement application 124. The server supplement application 124 may receive the genetic test results for the genetic test from the genetic laboratory device 138. Responsive to receiving the genetic test results, the server supplement application 124 may update the patient genetic data 128 based upon the genetic test results. More specifically, the server supplement application 124 can modify the patient genetic data 128 to include information regarding whether the patient has the variant form of the gene known to have the interaction with the medication.

The server supplement application 124 may repeat the above-described process for each medication taken by the patient to ensure genetic tests are ordered for variant forms of genes that are known to have interactions with medications that are currently taken or will be taken by the patient.

While the above-described functionality has been described as being provided by a supplement application executing on a server computing device separate from the computing device executing the server EHR 108, other possibilities are contemplated. For instance, the above-described functionality may be incorporated into a module of the server EHR 108.

Turning now to FIG. 3, an exemplary GUI 300 of the client supplement application 206 that can be presented on the display 208 of the client computing device 136 is illustrated. The GUI 300 may include a patient details field 302, a home button 304, a pharmacogenomics profile button 306, a genetic test results button 308, an orders button 310, an order genetic test button 312, and a pharmacogenomics profile 314. The patient details field 302 includes demographic information for the patient, such as a first and last name of the patient, a date of birth for the patient, a sex of the patient, and a medical records number (MRN) of the patient. When the GUI 300 receives a selection of the home button 304, the client computing device 136 may cause a GUI for the client EHR 304 to be shown on the display 208.

When the GUI 300 receives a selection of the pharmacogenomics profile button 306, the client supplement application 206 can display a pharmacogenomics profile 314 of the patient. The pharmacogenomics profile 314 of the patient includes medications of the patient (past and current) as well as identifiers for variant forms of genes (medication-gene pairings). As discussed above, some variant forms of genes may have an interaction with a medication. Each medication-gene pairing may include a visual marker, wherein the visual marker indicates whether or not the patient has undergone a genetic test for a gene having a variant form known to have an interaction with the medication. If the patient has undergone test for the gene having the variant form known to have an interaction with the medication, the visual marker may also indicate the severity of the interaction.

For instance, in the GUI 300, for medication 1, the patient has undergone a genetic test indicating that the patient possesses genetic variant 1C. The GUI 300 indicates that patients having genetic variant 1C have a significantly altered response to medication 1, thus the GUI 300 includes a "!!!" visual marker adjacent to the medication-gene pairing for medication 1. For medication 2, the patient has undergone a genetic test indicating that the patient possesses genetic variant 2B. The GUI 300 indicates that patients having genetic variant 2B have an altered response to medication 2, thus the GUI 300 includes a "!" visual marker adjacent to the medication-gene pairing for medication 2. The GUI 300 may also include selectable buttons ("View Guideline") that when selected, can cause guidelines for taking a medication when having the genetic variant known to have an interaction with the medication to be shown within the GUI 300.

For medication 3, the GUI 300 indicates that medication 3 is known to have an interaction with a variant form of a gene and that a genetic test for the variant form of the gene is available, but the patient has not yet undergone the genetic test. As such, the GUI 300 includes a "?" visual marker adjacent to the medication-gene pairing for medication 3. For medication 4, the GUI 300 indicates that medication 4 is known to have an interaction with a variant form of a gene and that the patient has undergone a genetic test for the variant form of the gene. The genetic test results for the genetic tests indicated that the patient had a variant of the gene not known to have an interaction with medication 4, hence, the GUI 300 includes a check mark adjacent to the gene-medication pairing for medication 4.

When the GUI 300 receives a selection of the order genetic tests button 312, the client supplement application 206 can transmit data to the server supplement application 124 causing the server supplement application 124 to construct an order for a genetic test for the variant form of the gene known to have an interaction with medication 3.

When the GUI 300 receives a selection of the genetic test results button 308, the GUI 300 can be updated to display genetic test results for genetic tests that the patient has undergone. When the GUI 300 receives a selection of the orders button 310, the GUI 300 can be updated to display details regarding genetic test orders that have been ordered for the patient.

Figure 4:
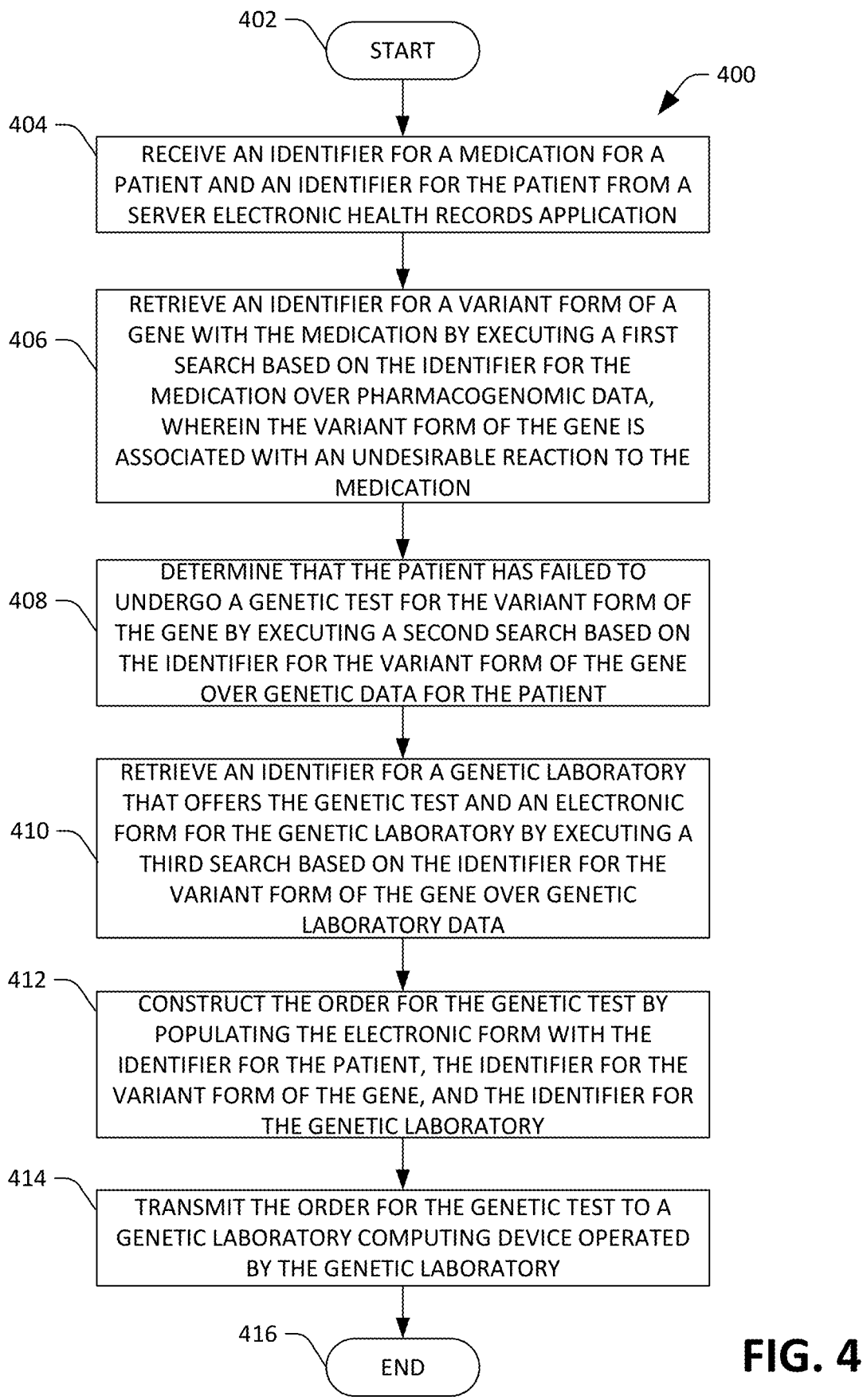
FIG. 4 is an exemplary methodology executed by a server supplement application for ordering a genetic test.
Figure 5:
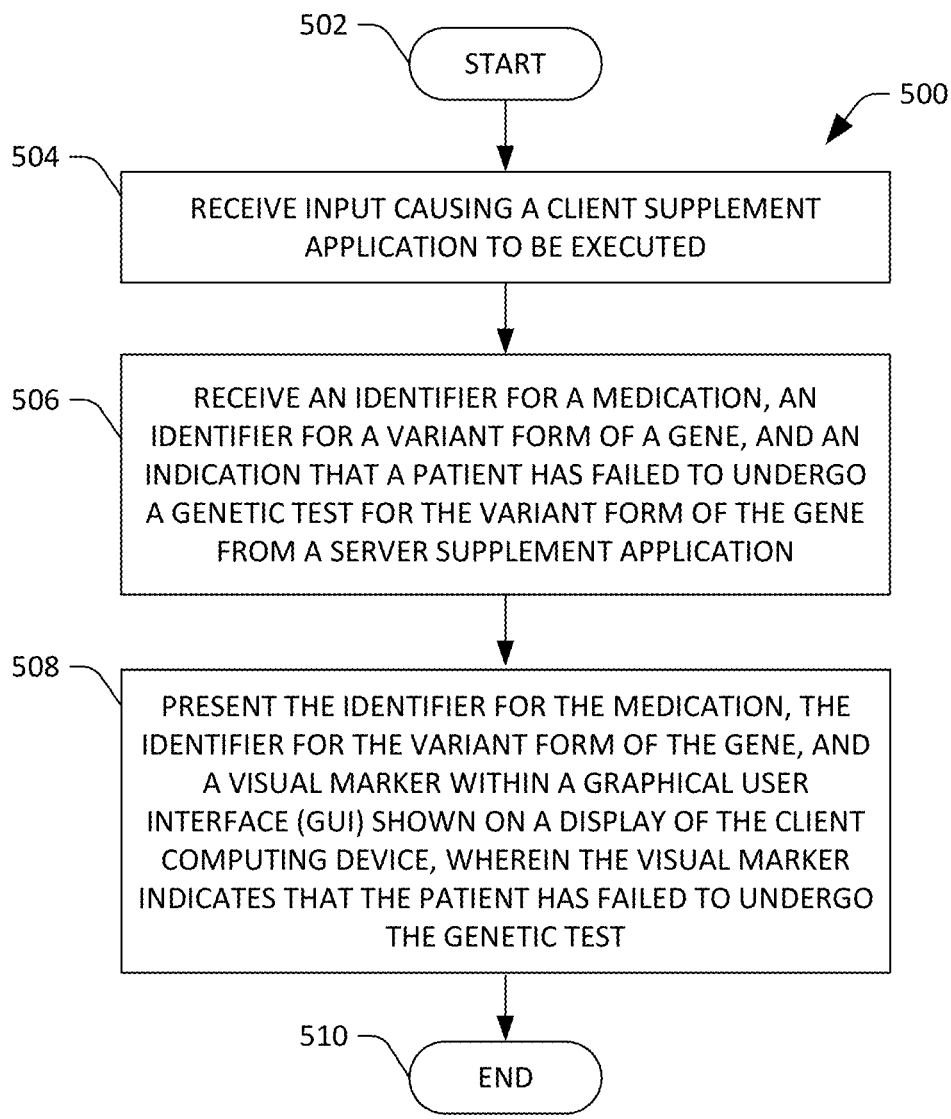
FIG. 5 is an exemplary methodology executed by a client supplement application for ordering a genetic test.

FIGS. 4 and 5 illustrate exemplary methodologies relating to ordering a genetic test. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring now to FIG. 4, a methodology 400 performed by a server computing device while the server computing device executes a server supplement application that facilitates ordering a genetic test for a variant form of a gene that has an interaction with a medication of a patient is illustrated. The methodology 400 begins at 402, and at 404 the server supplement application receives an identifier for a medication for a patient and an identifier for the patient from a server EHR executing on a second server computing device. At 406, the server supplement application retrieves an identifier for a variant form of a gene by executing a first search based on the identifier for the medication over pharmacogenomic data. The variant form of the gene is associated with an undesirable reaction to the medication. The pharmacogenomic data comprises interactions between a plurality of genes and a plurality of medications.

At 408, the server supplement application determines that the patient has failed to undergo a genetic test for the variant form of the gene by executing a second search based on the identifier for the variant form of the gene over genetic data for the patient. The genetic data for the patient comprises identifiers for variant forms of genes for which the patient has undergone testing. At 410, the server supplement application retrieves an identifier for a genetic laboratory that offers the genetic test and an electronic form for the genetic laboratory by executing a third search based on the identifier for the variant form of the gene over genetic laboratory data. The genetic laboratory data comprises identifiers for genetic laboratories and identifiers for genetic tests offered by the genetic laboratories. The genetic laboratory data also comprises electronic forms for ordering the genetic tests offered by the genetic laboratories, each form assigned to a different genetic laboratory.

At 412, the server supplement application constructs an order for the genetic test by populating the electronic form with the identifier for the patient, the identifier for the variant form of the gene, and the identifier for the genetic laboratory. At 414, the server supplement application transmits the order for the genetic test to a genetic laboratory computing device operated by the genetic laboratory. The methodology 400 concludes at 416.

With reference now to FIG. 5, a methodology 500 performed by a client computing device that facilitates ordering a genetic test for a variant form of a gene that has an interaction with a medication of a patient is illustrated. The methodology 500 begins at 502, and at 504 the client computing device receives input from a healthcare worker causing the client computing device to execute a client supplement application. At 506, the client supplement application executing on the client computing device receives an identifier for a medication, an identifier for the variant form of the gene, and an indication that a patient has failed to undergo a genetic test for the variant form of the gene from a server supplement application executing on a server computing device. At 508, responsive to receiving the identifier for the medication, the identifier for the variant form of the gene, and the indication that the patient has failed to undergo the genetic test, the client supplement application presents the identifier for the medication, the identifier for the variant form of the gene, and a visual marker indicating that the patient has failed to undergo the genetic test within a GUI shown on a display of the client computing device. The methodology 500 concludes at 510.

Figure 6:
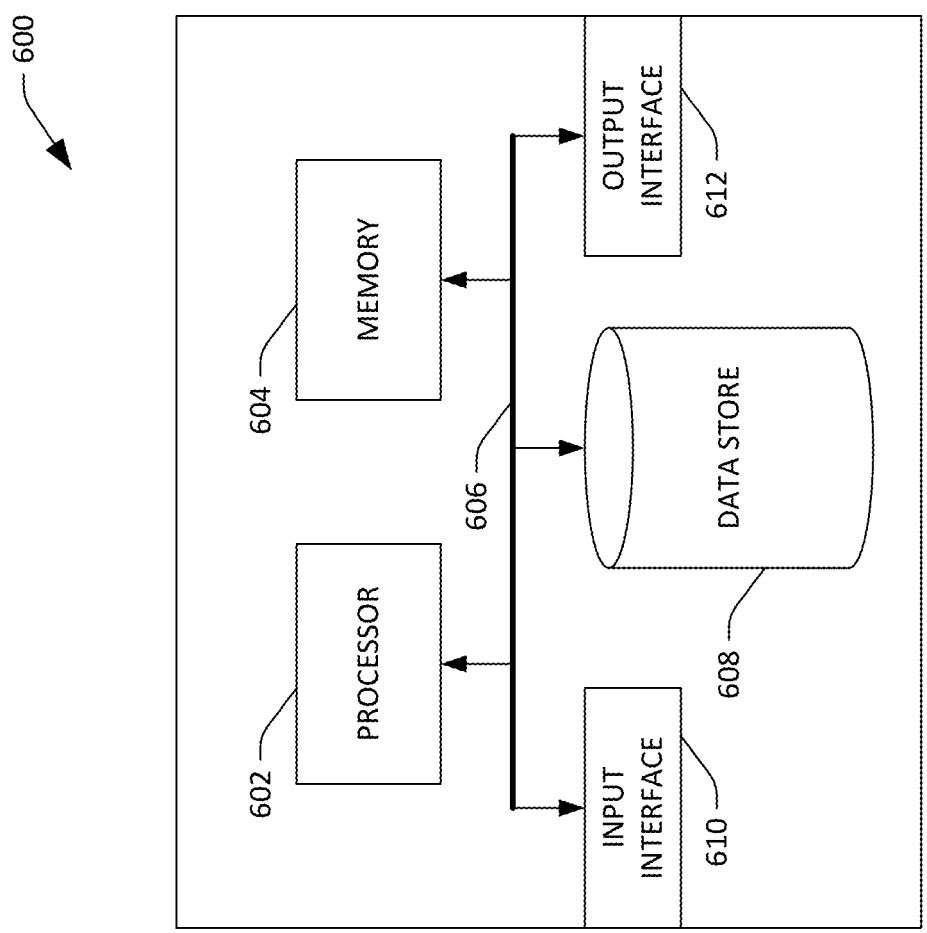
FIG. 6 is an exemplary computing system.

Referring now to FIG. 6, a high-level illustration of an exemplary computing device 600 that can be used in accordance with the systems and methodologies disclosed herein is illustrated. For instance, the computing device 600 may be used in a system that orders genetic tests. By way of another example, the computing device 600 can be used in a system that displays an identifier for a medication that is known to interact with a variant form of a gene. The computing device 600 includes at least one processor 602 that executes instructions that are stored in a memory 604. The instructions may be, for instance, instructions for implementing functionality described as being carried out by one or more components discussed above or instructions for implementing one or more of the methods described above. The processor 602 may access the memory 604 by way of a system bus 606. In addition to storing executable instructions, the memory 604 may also store patient genetic data, genetic laboratory data, genetic knowledge, etc.

The computing device 600 additionally includes a data store 608 that is accessible by the processor 602 by way of the system bus 606. The data store 608 may include executable instructions, patient genetic data, genetic laboratory data, genetic knowledge, etc. The computing device 600 also includes an input interface 610 that allows external devices to communicate with the computing device 600. For instance, the input interface 610 may be used to receive instructions from an external computer device, from a user, etc. The computing device 600 also includes an output interface 612 that interfaces the computing device 600 with one or more external devices. For example, the computing device 600 may display text, images, etc. by way of the output interface 612.

It is contemplated that the external devices that communicate with the computing device 600 via the input interface 610 and the output interface 612 can be included in an environment that provides substantially any type of user interface with which a user can interact. Examples of user interface types include graphical user interfaces, natural user interfaces, and so forth. For instance, a graphical user interface may accept input from a user employing input device(s) such as a keyboard, mouse, remote control, or the like and provide output on an output device such as a display. Further, a natural user interface may enable a user to interact with the computing device 600 in a manner free from constraints imposed by input device such as keyboards, mice, remote controls, and the like. Rather, a natural user interface can rely on speech recognition, touch and stylus recognition, gesture recognition both on screen and adjacent to the screen, air gestures, head and eye tracking, voice and speech, vision, touch, gestures, machine intelligence, and so forth.

Additionally, while illustrated as a single system, it is to be understood that the computing device 600 may be a distributed system. Thus, for instance, several devices may be in communication by way of a network connection and may collectively perform tasks described as being performed by the computing device 600.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

Alternatively, or in addition, the functionally described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

What has been described above includes examples of one or more embodiments. It is, of course, not possible to describe every conceivable modification and alteration of the above devices or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A server computing device comprising:
a processor; and
memory storing a server supplement application, wherein the server supplement application, when executed by the processor, is configured to perform acts comprising:
receiving an identifier for a medication for a patient and an identifier for the patient from a server electronic health records application (server EHR) executing on a second server computing device that is in network communication with the server computing device, wherein the server EHR causes the server supplement application to receive the identifier for the medication for the patient and the identifier for the patient responsive to receiving an indication from a client computing device that is in network communication with the server computing device and the second server computing device, the client computing device is operated by a healthcare worker;
executing a first search over computer-readable pharmacogenomic data stored in a computer-readable data store in order to retrieve an identifier for a variant form of a gene, the first search being based upon the identifier for the medication, wherein the computer-readable pharmacogenomic data comprises interactions between a plurality of genes and a plurality of medications, wherein the variant form of the gene is associated with an undesirable reaction to the medication;
executing a second search over computer-readable genetic data for the patient stored in the computer-readable data store in order to determine that the patient has failed to undergo a genetic test for the variant form of the gene, the second search being based upon the identifier for the variant form of the gene, wherein the computer-readable genetic data for the patient comprises identifiers for variant forms of genes for which the patient has undergone genetic testing, wherein the genetic test indicates whether the patient has the variant form of the gene;
responsive to determining that the patient has failed to undergo the genetic test, executing a third search over computer-readable genetic laboratory data stored in the computer-readable data store in order to retrieve an identifier for a genetic laboratory that offers the genetic test, wherein the computer-readable genetic laboratory data comprises identifiers for genetic laboratories and identifiers for genetic tests offered by the genetic laboratories;
transmitting the identifier for the genetic laboratory to a client supplement application executing on the client computing device, wherein the identifier for the genetic laboratory is presented on a display of the client computing device, wherein the client computing device receives a selection of the identifier for genetic laboratory;
upon receiving a notification from the client supplement application that the identifier for the genetic laboratory has been selected, constructing an electronic order for the genetic test using the identifier for the patient, the identifier for the variant form of the gene, and the identifier for the genetic laboratory, wherein constructing the electronic order for the genetic test occurs without receiving the identifier for the patient and the identifier for the variant form of the gene as input by the healthcare worker and comprises:
automatically retrieving an electronic form for the genetic test from the computer-readable genetic laboratory data, the electronic form is assigned to the genetic laboratory that is to perform the genetic test; and
automatically populating the electronic form with the identifier for the patient, the identifier for the variant form of the gene, and the identifier for the genetic laboratory;
transmitting the electronic order for the genetic test to a genetic laboratory computing device operated by the genetic laboratory, wherein the genetic laboratory computing device is in network communication with the server computing device;
upon receiving results for the genetic test from the genetic laboratory computing device, updating the computer-readable genetic data for the patient based upon the results; and
upon receiving an indication from the client supplement application or a second client supplement application executing on a second client computing device, transmitting data to the client supplement application or the second client supplement application, respectively, that causes a graphical user interface (GUI) to be displayed on the display or a second display of the second client computing device, respectively, wherein the GUI includes a pharmacogenomic profile that comprises a list of medications of the patient, wherein the list includes the medication for the patient, previous medications taken by the patient, and current medications taken by the patient, wherein each medication in the list of medications is marked with an indication in the GUI as to whether the patient has a normal or an altered response to each medication in the list of medications, the indication being based upon the computer-readable genetic data for the patient, and further wherein the pharmacogenomic profile is to be used to determine whether to prescribe the medication to the patient.

2. The server computing device of claim 1, wherein the computer-readable genetic laboratory data further comprises electronic forms for ordering the genetic tests, each electronic form assigned to a different genetic laboratory, wherein the electronic form for the genetic laboratory is included in the electronic forms.

3. The server computing device of claim 1, the acts further comprising:
subsequent to determining that the patient has failed to undergo the genetic test and prior to transmitting the electronic order for the genetic test to the genetic laboratory computing device, transmitting second data to the client supplement application, wherein the second data causes the client supplement application to present the identifier for the medication, the identifier for the variant form of the gene, and a visual marker on the display, wherein the visual marker indicates that the patient has failed to undergo the genetic test.

4. The server computing device of claim 3, wherein the client supplement application receives a selection of the identifier for the medication presented on the display, thereby causing the client supplement application to transmit a request for the interaction between the medication and the variant form of the gene to the server supplement application, the acts further comprising:
responsive to receiving the request for the interaction between the medication and the gene, retrieving the interaction from the computer-readable pharmacogenomic data; and
responsive to retrieving the interaction from the computer-readable pharmacogenomic data, transmitting the interaction to the client supplement application, wherein the interaction is presented on the display.

5. The server computing device of claim 4, wherein the interaction includes guidelines for using the medication when the patient has the variant form of the gene.

6. The server computing device of claim 1, wherein the client computing device executes a client electronic health records application (client EHR), wherein the client EHR transmits the indication to the server EHR causing the server EHR to transmit the identifier for the medication and the identifier for the patient to the server supplement application.

7. The server computing device of claim 1, wherein the medication is taken by the patient.

8. The server computing device of claim 1, wherein the medication is to be prescribed to the patient.

9. A method executed by a processor of a server computing device while the processor is executing a server supplement application, the method comprising:
receiving an identifier for a medication taken by a patient and an identifier for the patient from a server electronic health records application (server EHR) executing on a second server computing device that is in network communication with the server computing device, wherein the server EHR causes the server supplement application to receive the identifier for the medication for the patient and the identifier for the patient responsive to receiving an indication from a client computing device that is in network communication with the server computing device and the second server computing device, the client computing device is operated by a healthcare worker;
executing a first search over computer-readable pharmacogenomic data stored in a computer-readable data store in order to retrieve an identifier for a variant form of a gene, the first search being based upon the identifier for the medication, wherein the computer-readable pharmacogenomic data comprises interactions between a plurality of genes and a plurality of medications, wherein the variant form of the gene is associated with an undesirable reaction to the medication;
executing a second search over computer-readable genetic data for the patient stored in the computer-readable data store in order to determine that the patient has failed to undergo a genetic test for the variant form of the gene, wherein the computer-readable genetic data for the patient comprises identifiers for variant forms of genes for which the patient has undergone genetic testing, wherein the genetic test indicates whether the patient has the variant form of the gene; and
responsive to determining that the patient has failed to undergo the genetic test, executing a third search over computer-readable genetic laboratory data stored in the computer-readable data store in order to retrieve an identifier for a genetic laboratory that offers the genetic test wherein the computer-readable genetic laboratory data comprises identifiers for genetic laboratories and identifiers for genetic tests offered by the genetic laboratories;
transmitting the identifier for the genetic laboratory to a client supplement application executing on the client computing device, wherein the identifier for the genetic laboratory is presented on a display of the client computing device, wherein the client computing device receives a selection of the identifier for genetic laboratory;
upon receiving a notification from the client supplement application that the identifier for the genetic laboratory has been selected, constructing an electronic order for the genetic test by populating the electronic form with the identifier for the patient, the identifier for the variant form of the gene, and the identifier for the genetic laboratory, wherein constructing the electronic order for the genetic test occurs without receiving the identifier for the patient and the identifier for the variant form of the gene as input by the healthcare worker and comprises:
automatically retrieving an electronic form for the genetic test from the computer-readable genetic laboratory data, the electronic form is assigned to the genetic laboratory that is to perform the genetic test; and
automatically populating the electronic form with the identifier for the patient, the identifier for the variant form of the gene, and the identifier for the genetic laboratory;
transmitting the electronic order for the genetic test for the patient to a genetic laboratory computing device operated by the genetic laboratory, wherein the genetic laboratory computing device is in network communication with the server computing device;
upon receiving results for the genetic test from the genetic laboratory computing device, updating the computer-readable genetic data for the patient based upon the results; and
upon receiving an indication from the client supplement application or a second client supplement application executing on a second client computing device, transmitting data to the client supplement application or the second client supplement application, respectively, that causes a graphical user interface (GUI) to be displayed on the display or a second display of the second client computing device, respectively, wherein the GUI includes a pharmacogenomic profile that comprises a list of medications of the patient, wherein the list includes the medication for the patient, previous medications taken by the patient, and current medications taken by the patient, wherein each medication in the list of medications is marked with an indication in the GUI as to whether the patient has a normal or an altered response to each medication in the list of medications, the indication being based upon the computer-readable genetic data for the patient, and further wherein the pharmacogenomic profile is to be used to determine whether to prescribe the medication to the patient.

10. The method of claim 9, further comprising:
subsequent to determining that the patient has failed to undergo the genetic test and prior to transmitting the electronic order for the genetic test to the genetic laboratory computing device, transmitting second data to the client supplement application, wherein the second data causes the client supplement application to present the identifier for the medication, the identifier for the variant form of the gene, and a visual marker on the display, wherein the visual marker indicates that the patient has failed to undergo the genetic test.

11. The method of claim 10, wherein the client supplement application receives a selection of the identifier for the medication presented on the display, thereby causing the client supplement application to transmit a request for the interaction between the medication and the variant form of the gene to the server supplement application, the acts further comprising:
responsive to receiving the request for the interaction between the medication and the gene, retrieving the interaction from the computer-readable pharmacogenomic data; and
responsive to retrieving the interaction from the computer-readable pharmacogenomic data, transmitting the interaction to the client supplement application, wherein the interaction is presented on the display.

12. The method of claim 9, wherein the client computing device executes a client electronic health records application (client EHR), wherein the client EHR transmits the indication to the server EHR causing the server EHR to transmit the identifier for the medication and the identifier for the patient to the server supplement application.

13. The method of claim 9, wherein the computer-readable genetic laboratory data further comprises electronic forms for ordering the genetic tests, each electronic form assigned to a different genetic laboratory, wherein the electronic form for the genetic laboratory is included in the electronic forms.

14. The method of claim 11, wherein the interaction includes guidelines for using the medication when the patient has the variant form of the gene.

15. A non-transitory computer-readable storage medium comprising a server supplement application that, when executed by a processor of a server computing device, cause the processor to perform acts comprising:
responsive to receiving an identifier for a medication taken by a patient and an identifier for the patient from a server electronic health records application (server EHR) executing on a second server computing device that is in network communication with the server computing device, executing a first search over computer-readable pharmacogenomic data stored in a computer-readable data store in order to retrieve an identifier for a variant form of a gene, wherein the computer-readable pharmacogenomic data comprises interactions between a plurality of genes and a plurality of medications, wherein the variant form of the gene is associated with an undesirable reaction to the medication, wherein the server EHR causes the server supplement application to receive the identifier for the medication for the patient and the identifier for the patient responsive to receiving an indication from a client computing device that is in network communication with the server computing device and the second server computing device, the client computing device is operated by a healthcare worker;
executing a second search over computer-readable genetic data for the patient stored in the computer-readable data store in order to determine that the patient has failed to undergo a genetic test for the variant form of the gene, wherein the computer-readable genetic data for the patient comprises identifiers for variant forms of genes for which the patient has undergone genetic testing, wherein the genetic test indicates whether the patient has the variant form of the gene; and
responsive to determining that the patient has failed to undergo the genetic test, executing a third search over computer-readable genetic laboratory data stored in the computer-readable data store in order to retrieve an identifier for a genetic laboratory that offers the genetic test for the gene, wherein the computer-readable genetic laboratory data comprises identifiers for genetic laboratories and identifiers for genetic tests offered by the genetic laboratories;
transmitting the identifier for the genetic laboratory to a client supplement application executing on the client computing device, wherein the identifier for the genetic laboratory is presented on a display of the client computing device, wherein the client computing device receives a selection of the identifier for genetic laboratory;
upon receiving a notification from the client supplement application that the identifier for the genetic laboratory has been selected, constructing an electronic order for the genetic test using the identifier for the patient, the identifier for the variant form of the gene, and the identifier for the genetic laboratory, wherein constructing the electronic order for the genetic test occurs without receiving the identifier for the patient and the identifier for the variant form of the gene as input by the healthcare worker and comprises:
automatically retrieving an electronic form for the genetic test from the genetic laboratory data, the electronic form is assigned to the genetic laboratory that is to perform the genetic test; and
automatically populating the electronic form with the identifier for the patient, the identifier for the variant form of the gene, and the identifier for the genetic laboratory;
transmitting the electronic order for the genetic test to a genetic laboratory computing device operated by the genetic laboratory, wherein the genetic laboratory computing device is in network communication with the server computing device;
subsequent to transmitting the electronic order for the genetic test to the genetic laboratory computing device, receiving computer-readable genetic test results for the genetic test from the genetic laboratory computing device;
upon receiving results for the genetic test from the genetic laboratory computing device, updating the computer-readable genetic data for the patient based upon the results; and
upon receiving an indication from the client supplement application or a second client supplement application executing on a second client computing device, transmitting data to the client supplement application or the second client supplement application, respectively, that causes a graphical user interface (GUI) to be displayed on the display or a second display of the second client computing device, respectively, wherein the GUI includes a pharmacogenomic profile that comprises a list of medications of the patient, wherein the list includes the medication for the patient, previous medications taken by the patient, and current medications taken by the patient, wherein each medication in the list of medications is marked with an indication in the GUI as to whether the patient has a normal or an altered response to each medication in the list of medications, the indication being based upon the computer-readable genetic data for the patient, and further wherein the pharmacogenomic profile is to be used to determine whether to prescribe the medication to the patient.

16. The non-transitory computer-readable storage medium of claim 15, wherein the computer-readable genetic laboratory data further comprises electronic forms for ordering the genetic tests, each electronic form assigned to a different genetic laboratory, wherein the electronic form for the genetic laboratory is included in the electronic forms.

17. The non-transitory computer-readable storage medium of claim 15, the acts further comprising:
subsequent to determining that the patient has failed to undergo the genetic test and prior to transmitting the electronic order for the genetic test to the genetic laboratory computing device, transmitting second data to the client supplement application, wherein the second data causes the client supplement application to present the identifier for the medication, the identifier for the variant form of the gene, and a visual marker on the display, wherein the visual marker indicates that the patient has failed to undergo the genetic test.

18. The non-transitory computer-readable storage medium of claim 17, wherein the client supplement application receives a selection of the identifier for the medication presented on the display, thereby causing the client supplement application to transmit a request for the interaction between the medication and the variant form of the gene to the server supplement application, the acts further comprising:
responsive to receiving the request for the interaction between the medication and the gene, retrieving the interaction from the computer-readable pharmacogenomic data; and
responsive to retrieving the interaction from the computer-readable pharmacogenomic data, transmitting the interaction to the client supplement application, wherein the interaction is presented on the display.

19. The non-transitory computer-readable storage medium of claim 18, wherein the interaction includes guidelines for using the medication when the patient has the variant form of the gene.

20. The non-transitory computer-readable storage medium of claim 15, wherein the client computing device executes a client electronic health records application (client EHR), wherein the client EHR transmits the indication to the server EHR causing the server EHR to transmit the identifier for the medication and the identifier for the patient to the server supplement application.

* * * * *